(12) United States Patent
McGowan et al.

(10) Patent No.: US 9,284,304 B2
(45) Date of Patent: Mar. 15, 2016

(54) SUBSTITUTED PYRIMIDINES AS TOLL-LIKE RECEPTOR MODULATORS

(71) Applicant: JANSSEN SCIENCES IRELAND UC, Little Island, Co Cork (IE)

(72) Inventors: David Craig McGowan, Brussels (BE); Tim Hugo Maria Jonckers, Heist-op-den-Berg (BE); Pierre Jean-Marie Bernard Raboisson, Rosieres (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 14/420,066

(22) PCT Filed: Aug. 9, 2013

(86) PCT No.: PCT/EP2013/066673
§ 371 (c)(1),
(2) Date: Feb. 6, 2015

(87) PCT Pub. No.: WO2014/023813
PCT Pub. Date: Feb. 13, 2014

(65) Prior Publication Data
US 2015/0239872 A1    Aug. 27, 2015

(30) Foreign Application Priority Data
Aug. 10, 2012    (EP) .................................. 12180167

(51) Int. Cl.
*A61K 31/505* (2006.01)
*C07D 239/48* (2006.01)
*C07D 409/06* (2006.01)
*C07D 401/06* (2006.01)
*C07D 239/49* (2006.01)

(52) U.S. Cl.
CPC ............ *C07D 409/06* (2013.01); *C07D 239/48* (2013.01); *C07D 239/49* (2013.01); *C07D 401/06* (2013.01)

(58) Field of Classification Search
CPC ........................... A61K 31/505; C07D 239/48
USPC ............... 514/275; 544/323; 546/181, 268.1; 549/59
See application file for complete search history.

(56) References Cited

U.S. PATENT DOCUMENTS

| 6,028,076 A | 2/2000 | Hirota et al. |
| 6,329,381 B1 | 12/2001 | Kurimoto et al. |
| 6,951,866 B2 * | 10/2005 | Fujita et al. ................... 514/275 |

FOREIGN PATENT DOCUMENTS

| EP | 1110951 | 6/2001 |
| WO | WO00/06577 | 2/2000 |
| WO | WO 2006/117670 A1 | 11/2006 |
| WO | WO 2009/005687 A1 | 1/2009 |
| WO | WO 2009/067081 A1 | 5/2009 |
| WO | WO 2009/134624 A1 | 11/2009 |
| WO | WO2012/066335 | 5/2012 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Chawla, et al. Current Research & Information on Pharmaceutical Sciences (CRIPS), 5(1), 2004, 9-12.*
Hackam, et al. JAMA, 296(14), 2006, 1731-1732.*
Jules A. Hoffmann, "The Immune Response of *Drosophila*", Nature, 2003, vol. 426, Issue 6, pp. 33-38.
Christelle Moreau et al., "Synthesis of Cyclic Adenosine 5'-diphosphate Ribose Analogues: a C2' endo/syn "southern" Ribose Conformation Underlies Activity at the Sea Urchin cADPR Receptor", Organic & Biomolecular Chemistry, 2011, vol. 9, No. 1, pp. 278-290.
Kiyoshi Takeda, et al., "Toll-Like Receptors", Annu. Rev. Immunol., 2003, vol. 21, pp. 335-376.
Richard J. Ulevitch, "Therapeutics Targeting the Innate Immune System", Nature Reviews: Immunology, 2004, vol. 4, pp. 512-520.
International Search Report for Corresponding International Application PCT/EP2013/064763 Mailed on Aug. 7, 2013.
Vedantham, S., et al., Mechanism of Interferon Action in Hairy Cell Leukemia: A Model of Effective Cancer Biotherapy, Cancer Res. 1992, 52, 1056.
Hood, J. D. et al., Immunoprofiling toll-like receptor ligands Comparison of immunostimulatory and proinflammatory profiles in ex vivo human blood models, Hum. Vaccines 2010, 6,322-335.
Warshakoon, H, et al., Potential adjuvantic properties of innate immune stimuli, Hum. Vaccines 2009, 5, 381-394.
Grimm, M. et al., Toll-like receptor (TLR) 7 and TLR8 expression on CD133+ cells in colorectal cancer points to a specific role for inflammation induced TLRs in tumourigenesis and tumour progression, Eur. J. Cancer 46, (2010), 2849-57.
De Clercq, E.; et al., (S)-9-(2,3-Dihydroproply)adenine: An Aliphatic Nucleoside Analog with Broad-Spectrum Antiviral Activity, *Science* 1978, 200, 563-565.
Fried et. al. Peginterferon-alfa-2a plus ribavirin for chronic hepatitis C virus infection, *N Engl J Med* 2002; 347: 975-82.

* cited by examiner

*Primary Examiner* — Douglas M Willis

(57) ABSTRACT

This invention relates to alkylpyrimidine derivatives, processes for their preparation, pharmaceutical compositions, and their use in therapy.

6 Claims, No Drawings

SUBSTITUTED PYRIMIDINES AS TOLL-LIKE RECEPTOR MODULATORS

This application is a 35 U.S.C. §371 nationalization of PCT application PCT/EP2013/066673, filed Aug. 9, 2013, which claims priority to European patent application EP 12180167.4, filed Aug. 10, 2012, which are incorporated herein by reference.

BACKGROUND OF THE INVENTION

This invention relates to alkylpyrimidine derivatives, processes for their preparation, pharmaceutical compositions, and their use in treatment and/or therapy of diseases.

The present invention relates to the use of alkylpyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

A majority of mammalian species have between ten and fifteen types of Toll-like receptors. Thirteen TLRs (named simply TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as heterocyclic derivatives in WO2000006577, adenine derivatives in WO 98/01448 and WO 99/28321, and pyrimidines in WO 2009/067081.

In the treatment of certain viral infections, regular injections of interferon (IFNalfa) can be administered, as is the case for hepatitis C virus (HCV), (Fried et. al. Peginterferon-alfa plus ribavirin for chronic hepatitis C virus infection, *N Engl J Med* 2002; 347: 975-82). Orally available small molecule IFN inducers offer the potential advantages of reduced immunogenicity and convenience of administration. Thus, novel IFN inducers are potentially effective new class of drugs for treating virus infections. For an example in the literature of a small molecule IFN inducer having antiviral effect see De Clercq, E.; Descamps, J.; De Somer, P. *Science* 1978, 200, 563-565.

Interferon α is also given in combination with other drugs in the treatment of certain types of cancer (Eur. J. Cancer 46, 2849-57, and Cancer Res. 1992, 52, 1056). TLR 7/8 agonists are also of interest as vaccine adjuvants because of their ability to induce pronounced Th1 response (Hum. Vaccines 2010, 6, 322-335, and Hum. Vaccines 2009, 5, 381-394).

SUMMARY OF THE INVENTION

However, there exists a strong need for novel Toll-Like receptor modulators having preferred selectivity, and an improved safety profile compared to the compounds of the prior art.

In accordance with the present invention a compound of formula (I) is provided

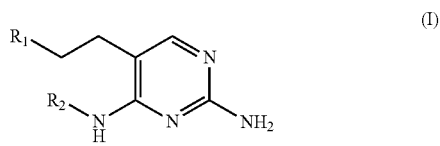

(I)

or a pharmaceutically acceptable salt, solvate or polymorph thereof, wherein $R_1$ is hydrogen, fluorine, hydroxyl, amine, $C_{1-6}$ alkyl, $C_{1-6}$ alkylamino, $C_{1-6}$ alkoxy, $C_{3-7}$ cycloalkyl, $C_{4-7}$ heterocycle, aryl, bicyclic heterocycle, arylalkyl, heteroaryl, heteroarylalkyl, aryloxy, heteroaryloxy, carboxylic acid, carboxylic ester, carboxylic amide each of which is optionally substituted by one or more substituents independently selected from halogen, hydroxyl, amino, $C_{1-6}$ alkyl, di-$(C_{1-6})$alkylamino, $(C_{1-4})$alkoxy-$(C_{1-4})$alkyl, $C_{1-6}$ alkylamino, $C_{1-6}$ alkyl, $C_{1-6}$ alkoxy, $C_{3-6}$ cycloalkyl, carboxylic acid, carboxylic ester, carboxylic amide, heterocycle, aryl, alkenyl, alkynyl, arylalkyl, heteroaryl, heteroarylalkyl, or nitrile, $R_2$ is $C_{1-6}$ alkyl, each of which is optionally substituted by one or more substituents independently selected from halogen, hydroxyl, amino, nitrile, carboxylic acid, carboxylic ester, carboxylic amide, $C_{1-3}$ alkyl, $C_{1-3}$ alkoxy or $C_{3-6}$ cycloalkyl, sulfone, sulfoxide, or nitrile, with the proviso that N-(2-amino-5-phenethylpyrimidine-4-yl)-N-pentylamine is excluded.

In a first embodiment the current invention relates to compounds of formula (I) wherein $R_1$ is a heterocycle and $R_2$ is $C_{1-6}$ alkyl substituted with, for example, a hydroxyl group.

In a second embodiment the present invention provides compounds of formula (I) wherein $R_1$ is hydrogen and wherein $R_2$ is $C_{1-6}$ alkyl, each of which is optionally substituted by one or more substituents independently selected from halogen, hydroxyl, amino, nitrile, carboxylic acid, carboxylic ester, carboxylic amide, $C_{1-3}$ alkyl, $C_{1-3}$ alkoxy or $C_{3-6}$ cycloalkyl, sulfone, sulfoxide, or nitrile.

The compounds of formula (I) and their pharmaceutically acceptable salt, solvate or polymorph thereof have activity as pharmaceuticals, in particular as modulators of Toll-Like Receptor (especially TLR7 and/or TLR8) activity.

In a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of any disorder in which the modulation of TLR7 and/or TLR8 is involved.

DETAILED DESCRIPTION OF THE INVENTION

The term "alkyl" refers to a straight-chain or branched-chain saturated aliphatic hydrocarbon containing the specified number of carbon atoms.

The term "halogen" refers to fluorine, chlorine, bromine or iodine.

The term "alkenyl" refers to an alkyl as defined above consisting of at least two carbon atoms and at least one carbon-carbon double bond.

The term "alkynyl" refers to an alkyl as defined above consisting of at least two carbon atoms and at least one carbon-carbon triple bond.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

The term "aryloxy" refers to an aromatic ring structure. Said aromatic group is singularly bonded to oxygen, like for instance phenol.

The term "heteroaryloxy" refers to an aromatic ring structure optionally comprising one or two heteroatoms selected from N, O and S. Said aromatic group, containing 5 to 7 ring atoms, one of which is singularly bonded to oxygen like for instance hydroxypyridine.

The term "bicyclic heterocycle" means an aromatic ring structure, as defined for the term "aryl" comprised of two fused aromatic rings. Each ring is optionally comprised of heteroatoms selected from N, O and S, in particular from N and O.

The term arylalkyl" means an aromatic ring structure as defined for the term "aryl" optionally substituted with an alkyl group.

The term "heteroarylalkyl" means an aromatic ring structure as defined for the term "heteroaryl" optionally substituted by an alkyl group.

"Heterocycle" refers to molecules that are saturated or partially saturated and include but are not limited to tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, morpholine, and cyclic sulfones.

"Heteroaryl" groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, furyl, oxazolyl, pyrrolyl, pyridonyl, pyridyl, pyridazinyl, pyrazinyl, thiophene or quinoline.

Pharmaceutically acceptable salts of the compounds of formula (I) include the acid addition and base salts thereof.

Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds

Compounds of formula (I) are prepared according to scheme 1.

Preparation of Example 1

Scheme 1:

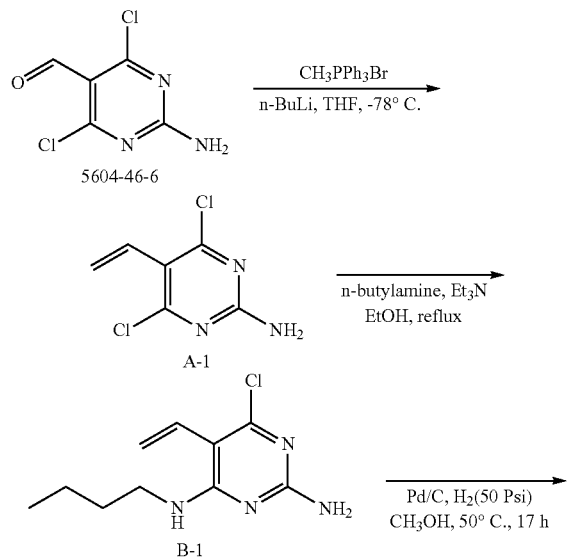

Synthesis of A-1

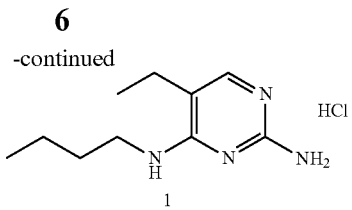

CH$_3$PPh$_3$Br (27.91 g, 78.1 mmol, 1.5 eq.) was suspended in THF (70 mL) and stirred at −78° C. under a N$_2$ atmosphere. n-butyllithium (30 mL, 75 mmol, 1.44 eq., 2.5 M in hexane) was added dropwise over 20 minutes and stirred for an additional 0.5 hours, followed by the addition of 2-amino-4,6-dichloro-5-formylpyrimidine [5604-46-6] (10.0 g, 52 mmol, 1.0 eq.) as a suspension in THF (180 mL). The cooling bath was removed and the mixture was stirred at room temperature for 2 hours. The reaction was cooled to −78° C. then NH$_4$Cl (sat., aq.) was added slowly. The cooling bath was removed and the mixture was stirred for 1.5 hours. The organic layer was separated, washed with water, dried (Na$_2$SO$_4$), the solids were removed by filtration, and the solvents of the filtrate were removed under reduced pressure. The crude was purified by silica column chromatography using a petroleum ether to ethyl acetate gradient to afford a colorless oil, A-1 (1.2 g).

$^1$H NMR (400 MHz, chloroform-d) δ ppm 5.30 (br. s., 2H), 5.65 (d, 1H), 5.82 (d, 1H), 6.58 (q, 1H)

Preparation of B-1

A-1 (1.0 g, 5.26 mmol), n-butylamine (0.39 g, 5.26 mmol) and Et$_3$N (0.53 g, 5.26 mmol, 1.0 eq.) in ethanol (10 mL) were refluxed for 12 hours. The solvent was removed under reduced pressure. The crude was purified by silica gel column chromatography using a petroleum ether to ethyl acetate gradient. The best fractions were pooled and concentrated under reduced pressure to give B-1 (300 mg).

LC-MS m/z=227 (M+H)

$^1$H NMR (400 MHz, CHLOROFORM-d) δ ppm 0.95 (t, J=7.3 Hz, 3H), 1.38 (dq, J=14.9, 7.4 Hz, 2H), 1.55 (quin, J=7.4 Hz, 2H), 3.38 (q, J=7.3 Hz, 2H), 4.75 (br. s., 2H), 5.39 (br. s., 1H), 5.5 (m, 2H), 6.55 (m, 1H)

Preparation of Example 1

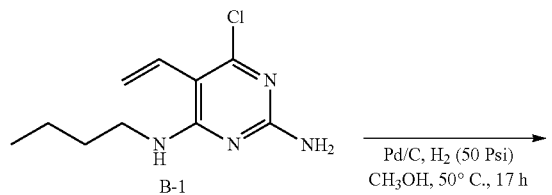

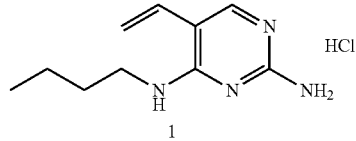

To a solution of B-1 (200 mg, 0.88 mmol, 1.0 eq.) in methanol (5 mL) was added 10% Pd/C (20 mg) and mixed with H$_2$ gas (50 Psi) at 50° C. for 17 hours. The crude product was purified by preparative high-performance liquid chromatography (C18 column, eluent: CH$_3$CN/H$_2$O from 10/90 to 95/5, 0.05% HCl). The desired fractions were pooled and concentrated under reduced pressure to afford 1 (74 mg).

LC-MS m/z=195 (M+H)

$^1$H NMR (400 MHz, CHLOROFORM-d) δ ppm 0.95 (t, J=7.3 Hz, 3H), 1.20 (t, J=7.3 Hz, 3H), 1.38 (dq, J=14.9, 7.4 Hz, 2H), 1.62 (quin, J=7.4 Hz, 2H), 1.93 (br. s., 1H), 2.37 (q, J=7.3 Hz, 2H), 3.40-3.63 (m, 2H), 6.18 (br. s., 1H), 7.24 (br. s., 1H), 13.43 (br. s., 1H)

TABLE 1

Compounds of formula (I). All compounds were synthesized according to the method to prepare example 1.

| # | STRUCTURE | H NMR | LC Method, Rt (min) | Mass Found (M + H) |
|---|---|---|---|---|
| 1 | 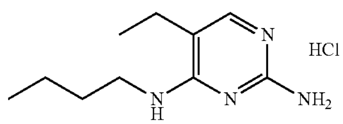 | $^1$H NMR (400 MHz, CHLOROFORM-d) δ ppm 0.95 (t, J = 7.3 Hz, 3 H), 1.20 (t, J = 7.3 Hz, 3 H), 1.38 (dq, J = 14.9, 7.4 Hz, 2 H), 1.62 (quin, J = 7.4 Hz, 2 H), 1.93 (br. s., 1 H), 2.37 (q, J = 7.3 Hz, 2 H), 3.40-3.63 (m, 2 H), 6.18 (br. s., 2 H), 7.24 (br. s., 1 H), 13.43 (br. s., 1 H) | 1, 3.86 | 195 |
| 2 | 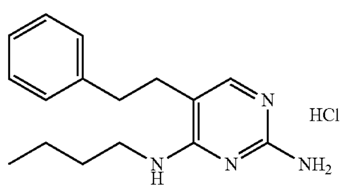 | $^1$H NMR (400 MHz, CHLOROFORM-d) δ ppm 0.95 (t, J = 7.3 Hz, 3 H), 1.20 (t, J = 7.3 Hz, 3 H), 1.38 (dq, J = 14.9, 7.4 Hz, 2 H), 1.62 (quin, J = 7.4 Hz, 2 H), 1.93 (br. s., 1 H), 2.37 (q, J = 7.3 Hz, 2 H), 3.40-3.63 (m, 2 H), 6.18 (br. s., 2 H), 7.24 (br. s., 1 H), 13.43 (br. s., 1 H) | 2, 3.6 | 271 |
| 3 | 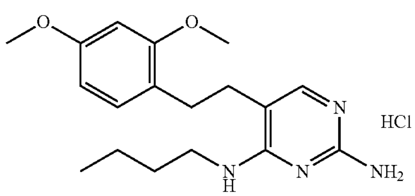 [SMILES: CCCCNc1nc(N)ncc1CCc1ccc(OC)cc1OC ; Cl] | $^1$H NMR (400 MHz, DMSO-d$_6$) δ ppm 0.92 (t, J = 7.3 Hz, 3 H), 1.26-1.38 (m, 2 H), 1.56 (t, J = 7.3 Hz, 2 H), 2.53-2.57 (m, 2 H), 2.63-2.72 (m, 2 H), 3.41-3.47 (m, 2 H), 3.71 (s, 3 H), 3.73 (s, 3 H), 6.46 (dd, J = 8.3, 2.5 Hz, 1 H), 6.51 (d, J = 2.3 Hz, 1 H), 7.02 (d, J = 8.3 Hz, 1 H), 7.24 (br. s., 1 H), 7.61 (br. s., 2 H), 8.15 (t, J = 5.6 Hz, 1 H), 11.85 (br. s., 1 H) | 2, 3.71 | 331 |
| 4 | 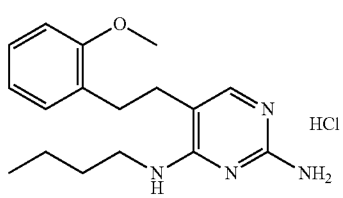 [SMILES: CCCCNc1nc(N)ncc1CCc1ccccc1OC ; Cl] | $^1$H NMR (400 MHz, DMSO-d$_6$) δ ppm 0.89 (t, J = 7.3 Hz, 3 H), 1.24-1.39 (m, 2 H), 1.54 (quin, J = 7.3 Hz, 2 H), 2.52-2.58 (m, 2 H), 2.69-2.78 (m, 2 H), 3.38-3.45 (m, 2 H), 3.71 (s, 3 H), 6.86 (t, J = 7.4 Hz, 1 H), 6.93 (d, J = 7.8 Hz, 1 H), 7.12 (dd, J = 7.3, 1.5 Hz, 1 H), 7.15-7.22 (m, 1 H), 7.26 (s, 1 H), 7.62 (br. s., 2 H), 8.16 (t, J = 5.5 Hz, 1 H), 12.01 (br. s., 1 H) | 2, 3.71 | 301 |
| 5 | 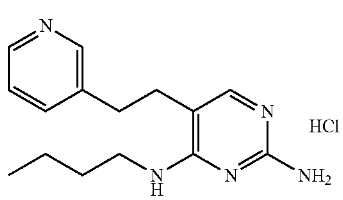 [SMILES: CCCCNc1nc(N)ncc1CCc1cccnc1 ; Cl] | $^1$H NMR (400 MHz, DMSO-d$_6$) δ ppm 0.91 (t, J = 7.3 Hz, 3 H), 1.22-1.39 (m, 2 H), 1.56 (t, J = 7.3 Hz, 2 H), 2.72-2.83 (m, 2 H), 2.91-3.04 (m, 2 H), 3.43 (q, J = 6.5 Hz, 2 H), 7.59 (s, 1 H), 7.72 (br. s., 2 H), 8.06 (dd, J = 8.0, 5.8 Hz, 1 H), 8.56-8.69 (m, 2 H), 8.83 (d, J = 5.3 Hz, 1 H), 9.03 (s, 1 H), 12.28 (br. s., 1 H) | 1, 3.34 | 272 |

TABLE 1-continued

Compounds of formula (I). All compounds were synthesized according to the method to prepare example 1.

| # | STRUCTURE | H NMR | LC Method, Rt (min) | Mass Found (M + H) |
|---|---|---|---|---|
| 6 | (pyridine-CH2CH2-pyrimidine with butyl-NH, NH2, HCl) | $^1$H NMR (400 MHz, DMSO-$d_6$) δ ppm 0.91 (t, J = 7.3 Hz, 3 H), 1.32 (sxt, J = 7.4 Hz, 2 H), 1.60 (quin, J = 7.3 Hz, 2 H), 2.85-2.96 (m, 2 H), 3.18-3.28 (m, 2 H), 3.45 (q, J = 6.8 Hz, 2 H), 7.65 (s, 1 H), 7.75 (br. s., 2 H), 7.95 (t, J = 6.4 Hz, 1 H), 8.06 (d, J = 8.0 Hz, 1 H), 8.56 (td, J = 7.8, 1.4 Hz, 1 H), 8.73 (t, J = 5.5 Hz, 1 H), 8.85 (d, J = 4.8 Hz, 1 H), 12.28 (br. s., 1 H) | 1, 3.33 | 272 |
| 7 | (quinoline-CH2CH2-pyrimidine with butyl-NH, NH2, HCl) | $^1$H NMR (300 MHz, DMSO-$d_6$) δ ppm 0.90 (t, J = 7.3 Hz, 3 H), 1.23-1.41 (m, 2 H), 1.57 (quin, J = 7.3 Hz, 2 H), 2.98 (t, J = 7.5 Hz, 2 H), 3.39 (d, J = 7.9 Hz, 2 H), 3.41-3.54 (m, 3 H), 7.64 (d, J = 4.9 Hz, 1 H), 7.70 (br. s., 1 H), 7.87 (d, J = 7.2 Hz, 1 H), 7.96 (br. s., 1 H), 8.07 (br. s., 1 H), 8.26 (d, J = 7.7 Hz, 1 H), 8.37 (br. s., 1 H), 8.61 (br. s., 1 H), 8.96 (br. s., 1 H), 12.03 (d, J = 4.3 Hz, 1 H) | 2, 2.54 | 322 |
| 8 | (thiophene-CH2CH2-pyrimidine with butyl-NH, NH2, HCl) | $^1$H NMR (400 MHz, DMSO-$d_6$) δ ppm 0.85-0.93 (m, 3 H), 1.23-1.35 (m, 2 H), 1.47-1.60 (m, 2 H), 2.63-2.72 (m, 2 H), 2.98 (t, J = 7.5 Hz, 2 H), 3.46 (br. s., 2 H), 6.88 (d, J = 3.3 Hz, 1 H), 6.94 (dd, J = 5.1, 3.4 Hz, 1 H), 7.32 (dd, J = 5.1, 1.1 Hz, 1 H), 7.43 (d, J = 5.3 Hz, 1 H), 7.59 (br. s., 2 H), 8.27 (t, J = 5.8 Hz, 1 H), 11.87 (d, J = 5.8 Hz, 1 H) | 1, 4.52 | 277 |

Analytical Methods. All compounds were characterized by LC-MS using the following methods:

Method 1. An Agilent 1100 LC-MS in positive ion mode was equipped with a YMC-PACK ODS-AQ, 50×2.0 mm, 5 μm column held at 50° C. The following mobile phase and gradient was used over a 10 minute total run time at 0.8 mL/min, monitoring at 220 nm:

| Mobile Phase | A: $H_2O$ (0.1% TFA) B: $CH_3CN$ (0.05% TFA) | | |
|---|---|---|---|
| | Time (min) | % A | % B |
| Gradient | 0 | 100 | 0 |
| | 1 | 100 | 0 |
| | 5 | 40 | 60 |
| | 7.5 | 40 | 60 |
| | 8 | 100 | 0 |

Method 2. An Agilent 1100 LC-MS in positive ion mode was equipped with a YMC-PACK ODS-AQ, 50×2.0 mm, 5 μm column held at 50° C. The following mobile phase and gradient was used over a 10 minute total run time at 0.8 mL/min, monitoring at 220 nm:

| Mobile Phase | A: $H_2O$ (0.1% TFA) B: $CH_3CN$ (0.05% TFA) | | |
|---|---|---|---|
| | Time (min) | % A | % B |
| | 0 | 90 | 10 |
| | 0.8 | 90 | 10 |
| | 4.5 | 20 | 80 |
| | 7.5 | 20 | 80 |
| | 8 | 90 | 10 |

Biological Activity of Compounds of Formula (I)

Description of Biological Assays

Assessment of TLR 7 and TLR 8 Activity

The ability of compounds to activate human TLR7 (hTLR7) and/or TLR8 (hTLR8) was assessed in a cellular reporter assay using HEK293 cells transiently transfected with a TLR7 or TLR8 expression vector and NFκB-luc reporter construct. In one instance the TLR expression construct expresses the respective wild type sequence or a mutant sequence comprising a deletion in the second leucine-rich repeat of the TLR. Such mutant TLR proteins have previously been shown to be more susceptible to agonist activation (U.S. Pat. No. 7,498,409).

Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated overnight at 37° C. in a humidified 5% $CO_2$ atmosphere. Transfected cells were then detached with Trypsin-EDTA, washed in PBS and resuspended in medium to a density of $1.67×10^5$ cells/mL. Thirty microliters of cells were then dispensed into each well in 384-well plates, where 10 μL of compound in 4% DMSO was already present. Following 48 hours incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

In parallel, a similar dilution series of compound was used (10 μL of compound in 4% DMSO) with 30 μL per well of cells transfected with NFκB-luc reporter construct alone (1.67×10$^5$ cells/mL). Six hours after incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

All compounds showed CC50 of >24 μM in the HEK 293 TOX assay described above.

| # | STRUCTURE | hTLR7 wt (LEC) | hTLR8 wt (LEC) |
|---|---|---|---|
| 1 | 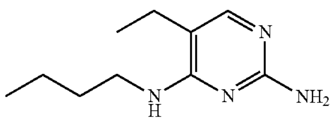 | 2.4 | 1.3 |
| 2 | 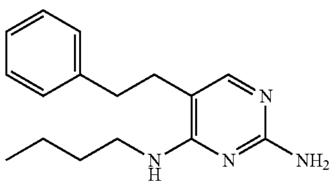 [SMILES: CCCCNc1nc(N)ncc1CCc1ccccc1] | 6.7 | 6.5 |
| 3 | 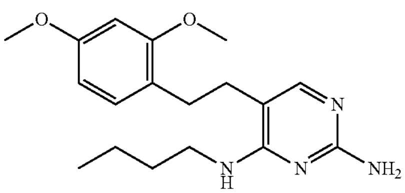 [SMILES: CCCCNc1nc(N)ncc1CCc1ccc(OC)cc1OC] | 2.4 | 12 |
| 4 | 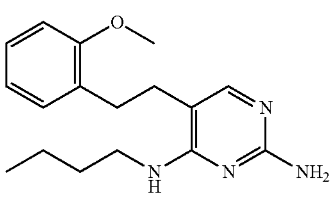 [SMILES: CCCCNc1nc(N)ncc1CCc1ccccc1OC] | 5 | 13 |
| 5 | 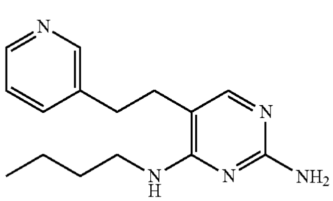 [SMILES: CCCCNc1nc(N)ncc1CCc1cccnc1] | 1.2 | 1.4 |
| 6 | 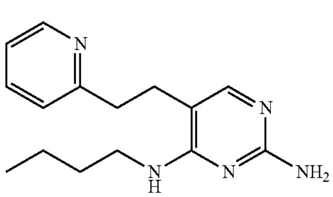 [SMILES: CCCCNc1nc(N)ncc1CCc1ccccn1] | 0.6 | 1.6 |
| 7 | | 0.5 | 1.2 |
| 8 | | 8.1 | 3.6 |

The invention claimed is:

1. A compound of formula (I)

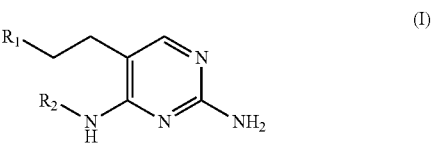

or a pharmaceutically acceptable salt thereof, wherein
$R_1$ is hydrogen, fluoro, hydroxy, amino, $C_{1-6}$ alkyl, $C_{1-6}$ alkylamino, $C_{1-6}$ alkoxy, $C_{3-7}$ cycloalkyl, $C_{4-7}$ heterocyclyl, aryl, bicyclic heterocyclyl, arylalkyl, heteroaryl, heteroarylalkyl, aryloxy, heteroaryloxy, carboxy, carboxy ester, or amido each of which is optionally substituted by one or more substituents independently selected from halo, hydroxy, amino, di-($C_{1-6}$)alkylamino, ($C_{1-4}$) alkoxy-($C_{1-4}$)alkyl, $C_{1-6}$ alkylamino, $C_{1-6}$ alkyl, $C_{1-6}$ alkoxy, $C_{3-6}$ cycloalkyl, carboxy, carboxy ester, amido, heterocyclyl, aryl, alkenyl, alkynyl, arylalkyl, heteroaryl, heteroarylalkyl, or cyano,
$R_2$ is $C_{1-6}$ alkyl, which is optionally substituted by one or more substituents independently selected from halo, hydroxy, amino, cyano, carboxy, carboxy ester, amido, $C_{1-3}$ alkyl, $C_{1-3}$ alkoxy or $C_{3-6}$ cycloalkyl,
with the proviso that N-(2-amino-5-phenethylpyrimidin-4-yl)-N-pentylamine is excluded.

2. A compound of formula (I)

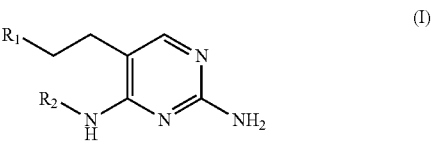

or a pharmaceutically acceptable salt thereof, wherein
$R_1$ is a heterocyclyl, and
$R_2$ is $C_{1-6}$ alkyl substituted by one or more hydroxy.

3. The compound as claimed in claim 1, wherein
$R_1$ is hydrogen, and

R₂ is optionally substituted by one or more substituents independently selected from halo, hydroxy, amino, cyano, carboxy, carboxy ester, amido, $C_{1-3}$ alkyl, $C_{1-3}$ alkoxy, or $C_{3-6}$ cycloalkyl.

4. A pharmaceutical composition comprising a compound as claimed in claim 1 or a pharmaceutically acceptable salt thereof together with one or more pharmaceutically acceptable excipients, diluents or carriers.

5. A method for modulating toll-like receptor 7 activity and/or toll-like receptor 8 activity in a human, comprising administering to said human a therapeutically effective amount of at least one compound as claimed in claim 1.

6. A compound selected from the group consisting of:

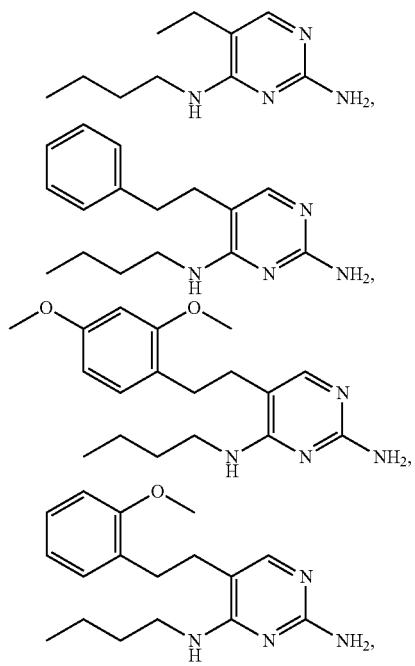

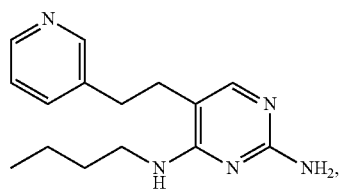

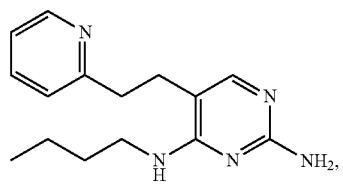

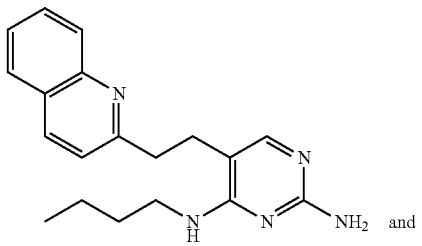 and

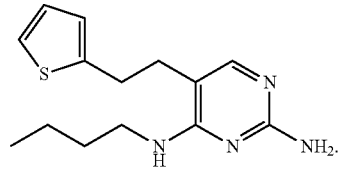

* * * * *